United States Patent [19]

Becuwe et al.

[11] 4,145,361
[45] Mar. 20, 1979

[54] 2-FLUORO-2,2-DINITROETHYL/SUBSTITUTED ARYL CARBONATES AND PROCESS FOR THEIR PREPARATION

[75] Inventors: Alain G. Becuwe, Mennecy; Claude M. Ucciani, Vert le Petit, both of France

[73] Assignee: Societe Nationale des Poudres et Explosifs, Paris Cedex, France

[21] Appl. No.: 858,688

[22] Filed: Dec. 8, 1977

[30] Foreign Application Priority Data

Dec. 30, 1976 [FR] France .................. 76 39521

[51] Int. Cl.² .................. C07C 69/96
[52] U.S. Cl. .................. 260/463; 149/105
[58] Field of Search .......... 149/105; 260/463

[56] References Cited

U.S. PATENT DOCUMENTS

| 3,576,840 | 4/1971 | Frankel et al. | 149/105 |
| 3,624,129 | 11/1971 | Kamley | 149/105 |

Primary Examiner—Leland A. Sebastian
Attorney, Agent, or Firm—Bucknam and Archer

[57] ABSTRACT

Carbonates of 2-fluoro-2,2-dinitroethyl and of a substituted aryl are described of the general formula

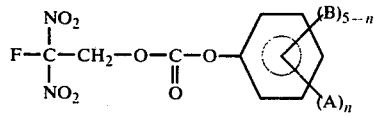

in which B is hydrogen or methyl, A is nitro or trifluoromethyl and n is an integer number between 2 and 4. The preparation involves reacting 2-fluoro-2,2-dinitroethyl chloroformate with an alkali metal phenate of the formula

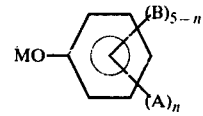

in which M = Na or K, A, B and n have the same meaning as hereinabove, at between 10° and 50° C. in an anhydrous aprotic polar solvent medium.

5 Claims, No Drawings

2-FLUORO-2,2-DINITROETHYL/SUBSTITUTED ARYL CARBONATES AND PROCESS FOR THEIR PREPARATION

The invention relates to 2-fluoro-2,2-dinitroethyl/-substituted aryl carbonates and a process for their preparation.

The carbonates according to the invention have the general formula

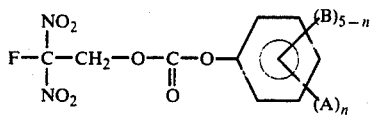

in which B = H or $CH_3$, and $(A)_n$ = 2 to 4 $NO_2$ and/or $CF_3$ groups.

They are prepared by the action of 2-fluoro-2,2-dinitroethyl chloroformate on the corresponding alkali metal phenate, at between 10° and 50° C., in an anhydrous aprotic polar medium.

Application: the new compounds are useful as explosives and energy-producing additives, especially the mixed carbonate of 2-fluoro-2,2-dinitroethyl and 2,4,6-trinitrophenyl.

The present invention relates to a process for the preparation of a carbonate of 2-fluoro-2,2-dinitroethyl and an aryl which is substituted by electron-attracting groups, as well as to these compounds as new industrial products.

For several years, the fluoro-nitrated derivatives, and particularly those which carry the 2-fluoro-2,2-dinitroethyl group, have aroused a growing interest in the field of high-performance explosives, binders and energy-producing plasticisers.

Numerous contributions have recently been provided concerning the preparation of these compounds which carry at least one 2-fluoro-2,2-dinitroethyl group. U.S. Pat. Nos. 3,544,630 and 3,873,617 thus describe processes for the preparation of primary and secondary amines, respectively, which contain the said group, whereas processes for the synthesis of useful intermediates, namely 2-fluoro-2,2-dinitroethyl chloroformate and isocyanate, have been described in U.S. Pat. No. 3,560,547 and by ADOLPH in Journal of Organic Chemistry, Vol. 37, No. 5, page 747 et seq. in 1972. The Applicant Company has herself proposed, in her French Patent Application Nos. 75/31,025 and 75/39,426, original processes, giving high yields, for synthesising these two important intermediates.

However, with regard to a carbonate carrying the 2-fluoro-2,2-dinitroethyl group, those skilled in the art have much less information at their disposal. In fact, even though U.S. Pat. No. 3,431,290 of HALL does describe a process for the synthesis of bis-(2-fluoro-2,2-dinitroethyl)-carbonate, which process consists in reacting phosgene with 2-fluoro-2,2-dinitroethanol in the presence of pyridine N-oxide, the synthesis of mixed carbonates is obviously not possible by this process.

However, it might be possible to consider using the general method of synthesis of mixed carbonates, which method consists in reacting the chloroformate of a first group with the alcohol of a second group, in the presence of an acid acceptor, in order to obtain the carbonate of the two said groups. Nevertheless, a reaction of this kind is difficult to carry out in the case of 2-fluoro-2,2-dinitroethyl chloroformate because of the electron-attracting character of this group, which renders the carbonate obtained very sensitive to hydrolysis.

Furthermore, if the second group is also electron-attracting, the preceding method of synthesis fails completely.

The Applicant Company has now discovered a process for the preparation of a mixed carbonate of 2-fluoro-2,2-dinitroethyl and an aryl which is substituted at least by electron-attracting groups, which process is characterised in that 2-fluoro-2,2-dinitroethyl chloroformate is reacted with an alkali metal phenate substituted by electron-attracting groups, at between 10° and 50° C. in a perfectly anhydrous aprotic polar solvent medium.

The general equation of the reaction of the process according to the invention is written:

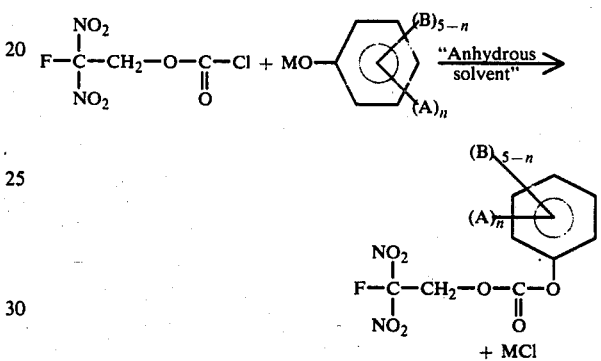

in which M is sodium or potassium, $(A)_n$ represents from two to four identical or different electron-attracting groups chosen from the group comprising nitro and trifluoromethyl groups, and B is a hydrogen atom or an electron-donating group such as a methyl group.

Amongst the anhydrous aprotic polar solvents which can be used within the scope of the present invention, a mixture of acetone and methylene chloride is particularly preferred.

The order in which the reactants are introduced is of little importance; however, it is preferred to introduce the 2-fluoro-2,2-dinitroethyl chloroformate solution into the alkali metal phenate solution, the latter being optionally a partial solution at the start.

The reaction is carried out at between 10° and 50°C. and accelerates with increasing temperature. There is a real danger of explosion above 50° C.

Amongst the alkali metal phenates substituted by electron-attracting groups, which phenates can be used within the scope of the present invention, there may be mentioned, for example, the sodium or potassium salts of the following phenols: picric acid, 2,6-dinitrophenol, 2,6-dinitro-4-trifluoromethylphenol, 2-nitro-4,6-di-(trifluoromethyl)-phenol, 2,4,6-tri-(trifluoromethyl)-phenol and 2-trifluoromethyl-3-methyl-4,6-dinitrophenol.

Therefore, the invention also relates to the carbonates of the general formula:

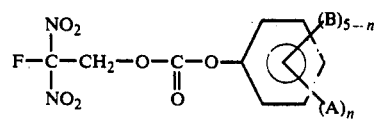

as new industrial products, in which formula $(A)_n$ represents from two to four identical or different electron-attracting groups chosen from the group comprising nitro and trifluoromethyl groups, and B is a hydrogen atom or an electron-donating group such as a methyl group.

These compounds are useful as explosives and as energy-producing additives for propellants.

Amongst the new compounds which can be achieved by the invention, 2-fluoro-2,2-dinitroethyl 2,4,6-trinitrophenyl carbonate is particularly valuable as an explosive.

By virtue of its high oxygen balance ($-13.5\%/CO$) (compared with $-24.6\%/CO$ for TNT) for a molecule having a high molecular weight (M = 400 g), and of its melting point of about 100° C. (M.p. = 97° C.), this compound can be advantageously used as a castable explosive.

EXAMPLE

The synthesis of 2-fluoro-2,2-dinitroethyl 2,4,6-trinitrophenyl carbonate was carried out, this being a compound which carries a high number of electron-attracting groups, and the synthesis of which is not possible by means of the conventional processes.

5.34 g of potassium picrate and 40 ml of anhydrous acetone were introduced into a reactor; dissolution is only partial.

A solution of 0.02 mol (4.4 g) of 2-fluoro-2,2-dinitroethyl chloroformate in 12.5 ml of methylene chloride is rapidly run into the solution. The reaction mixture assumes a green colour.

After heating for 5 hours at the reflux temperature of the solvent, the mixture is allowed to return to ambient temperature, after which the insoluble materials are removed by filtration and the solvent is removed by evaporation.

A pasty residue is obtained which, after dissolution in ethyl ether, is then treated with animal charcoal.

By filtration of the ethereal solution, 1 g of yellow crystals (yield 12.4%), which have a melting point of 97° C. after drying in vacuo, is recovered.

These yellow crystals are identified by the following analyses as indeed being the expected carbonate in the pure state:

Thin layer chromatography (eluent: toluene/acetone in the ratio 9/1): 1 single spot infra-red spectrum (KBr disc): $\nu C = O$ of the carbonates at 1,805 cm$^{-1}$

| elementary analysis | | | | |
|---|---|---|---|---|
| | C % | H % | N % | F % |
| Calculated | 26.4 | 0.98 | 17.1 | 4.65 |
| Found | 26.6 | 0.98 | 17.3 | 4.68 |

We claim:
1. Process for the synthesis of mixed carbonates of 2-fluoro-2,2-dinitroethyl and of an aryl substituted at least by electron-attracting groups, wherein 2-fluoro-2,2-dinitroethyl chloroformate is reacted with an alkali metal phenate of the formula

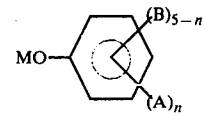

in which M = Na or K, B is hydrogen or methyl and A is nitro or trifluoromethyl, n is an integer number between 2 and 4, at between 10° and 50° C. in an anhydrous aprotic polar solvent medium.

2. Process of synthesis according to claim 1, wherein the anhydrous aprotic polar solvent medium is a mixture of anhydrous methylene chloride and anhydrous acetone.

3. Process of synthesis according to any one of claims 1 or 2, wherein the alkali metal phenate is sodium or potassium picrate.

4. Carbonates of 2-fluoro-2,2-dinitroethyl and of a substituted aryl of the general formula:

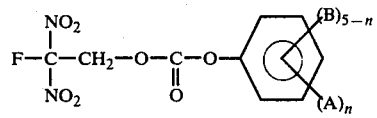

in which B is hydrogen or methyl and A is nitro or trifluoromethyl and n is an integer number between 2 and 4.

5. 2-Fluoro-2,2-dinitroethyl 2,4,6-trinitrophenyl carbonate.

* * * * *